United States Patent
Hasumi et al.

(12)

(10) Patent No.: US 11,504,467 B2
(45) Date of Patent: Nov. 22, 2022

(54) LIQUID INJECTION DEVICE AND ASSEMBLY INCLUDING SAME

(71) Applicant: TERUMO KABUSHIKI KAISHA, Tokyo (JP)

(72) Inventors: Kiyoaki Hasumi, Yamanashi (JP); Eiji Suzuki, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/983,348

(22) Filed: Aug. 3, 2020

(65) Prior Publication Data

US 2020/0360597 A1  Nov. 19, 2020

Related U.S. Application Data (60) Division of application No. 15/424,472, filed on Feb. 3, 2017, now abandoned, which is a continuation of
(Continued)

(30) Foreign Application Priority Data

Aug. 6, 2014 (JP) ................................. 2014-160830

(51) Int. Cl.
  *A61M 5/00* (2006.01)
  *A61M 5/20* (2006.01)
  (Continued)

(52) U.S. Cl.
  CPC .......... *A61M 5/002* (2013.01); *A61M 5/2033* (2013.01); *A61M 5/3202* (2013.01);
  (Continued)

(58) Field of Classification Search
  CPC .. A61M 5/002; A61M 5/2033; A61M 5/3202; A61M 5/3204; A61M 5/008; A61M 5/178; A61M 2005/2013; B65D 75/36
  (Continued)

(56) References Cited

U.S. PATENT DOCUMENTS 4,596,562 A  6/1986  Vernon
4,844,249 A  7/1989  Coulombe
(Continued)

FOREIGN PATENT DOCUMENTS

JP  2006-182448 A  7/2006
JP  2007-536047 A  12/2007
(Continued)

OTHER PUBLICATIONS

International Searching Authority, "International Search Report," issued in connection with International Patent Application No. PCT/JP2015/072252, dated Nov. 2, 2015.
International Searcning Autnority, "Written Opinion", issued in connection with International Patent Application No. PCT/JP2015/072252, dated Nov. 2, 2015.
(Continued)

*Primary Examiner* — Jacob K Ackun
(74) *Attorney, Agent, or Firm* — Foley & Lardner LLP (57) ABSTRACT

A liquid injection device includes: a syringe that comprises a barrel part configured to be filled with a liquid, and a needle attached to a distal portion of the barrel part and configured to discharge the liquid, a cap that covers the needle; a housing that covers at least a base end part of the syringe; and a step part that is formed on an outer peripheral surface of the cap or between the housing and the cap, the step part protruding farther outward than a side surface of the barrel part. The step part is configured to engage with a lower surface of a notch part that extends laterally inward from an outer edge of a flange part of a container such that the cap is removable from the housing by the notch part.

6 Claims, 9 Drawing Sheets

Related U.S. Application Data application No. PCT/JP2015/072252, filed on Aug. 5, 2015.

(51) Int. Cl.
*A61M 5/32* (2006.01)
*B65D 75/36* (2006.01)
*A61M 5/178* (2006.01)

(52) U.S. Cl.
CPC ........... *A61M 5/3204* (2013.01); *B65D 75/36* (2013.01); *A61M 5/008* (2013.01); *A61M 5/178* (2013.01); *A61M 2005/2013* (2013.01)

(58) Field of Classification Search
USPC ................................................ 206/363, 364
See application file for complete search history.

(56) References Cited

U.S. PATENT DOCUMENTS

| | | | |
|---|---|---|---|
| 4,984,686 A * | 1/1991 | Shillington | A61M 5/3205 220/908 |
| 5,007,535 A | 4/1991 | Meseke et al. | |
| 5,024,327 A | 6/1991 | Shillington | |
| 5,564,565 A | 10/1996 | Yamada | |
| 6,228,324 B1 | 5/2001 | Hasegawa et al. | |
| 6,257,408 B1 | 7/2001 | Odierno | |
| 6,279,743 B1 * | 8/2001 | Ballard | A61M 5/3204 211/70.6 |
| 7,850,646 B2 | 12/2010 | Segal | |
| 8,240,468 B2 | 8/2012 | Wilkinson et al. | |
| 8,303,599 B2 | 11/2012 | Hess et al. | |
| 2002/0195362 A1 | 12/2002 | Abe | |
| 2004/0069667 A1 | 4/2004 | Tomellini et al. | |
| 2005/0269227 A1 | 12/2005 | Erickson et al. | |
| 2006/0169611 A1 | 8/2006 | Prindle | |
| 2014/0013718 A1 | 1/2014 | Maasarani | |
| 2014/0224688 A1 | 8/2014 | Slemmen et al. | |

FOREIGN PATENT DOCUMENTS

| | | |
|---|---|---|
| JP | 2011-139755 A | 7/2011 |
| JP | 5487489 B2 | 5/2014 |
| WO | WO-2012/137803 A1 | 10/2012 |
| WO | WO-2014/045336 A1 | 3/2014 |

OTHER PUBLICATIONS

International Searching Authority, "International Preliminary Report on Patentability," issued in connection with International Patent Application No. PCT/JP2015/072252, dated Feb. 7, 2017.

Office Action issued in the corresponding JP Patent Application Ser. No. 2016-540270, dated May 7, 2019.

* cited by examiner

LIQUID INJECTION DEVICE AND ASSEMBLY INCLUDING SAME

CROSS-REFERENCE TO RELATED APPLICATIONS

The present application is a Divisional of U.S. patent application Ser. No. 15/424,472, filed on Feb. 3, 2017, which is a Bypass Continuation of PCT Application No. PCT/JP2015/072252, filed on Aug. 5, 2015, which claims priority to Japanese Application number 2014-160830, filed on Aug. 6, 2014. The contents of these applications are hereby incorporated by reference in their entireties.

BACKGROUND

The present disclosure relates to a packaging body and a packaging assembly.

One known liquid injection device is an auto injector, in which a plunger is pressurized in a distal direction by a biasing force of a coil spring and the plunger then automatically moves toward the distal direction in administering a drug solution to a living body (see, for example, WO 2012/137803). A cap is removably attached to the distal portion of the liquid injection device, and thus, a hollow needle in the liquid injection device can be protected, and erroneous pricking by the hollow needle and the like can be prevented. According to this liquid injection device, even a person having a weak grip such as an aged person or a person who has difficulty in the fingers such as a patient suffering from rheumatism can administer a drug solution in an easy and certain way.

Such liquid injection device is housed in, for example, the blister packaging body described in JP 2007-536047 A, or the like. Thus, the liquid injection device can be protected during transport, the transpiration of the moisture in the drug solution from the liquid injection device can be prevented, and a sterile state around the liquid injection device can be maintained. In using the liquid injection device, the liquid injection device is taken out of the packaging body, and the cap attached to the distal end is removed by pinching with fingers.

However, there is a problem that is it difficult for a person having a weak grip, such as an aged person or a person who has difficulty in the fingers such as a patient suffering from rheumatism, to remove the cap by pinching with the fingers.

SUMMARY

One object of certain embodiments of the present invention is to provide a liquid injection device and an assembly including the same, which enable easy removal of a cap of the liquid injection device, such as an auto injector housed in the packaging body or packaging assembly.

In one embodiment, a liquid injection device includes: a syringe that comprises a barrel part configured to be filled with a liquid, and a needle attached to a distal portion of the barrel part and configured to discharge the liquid, a cap that covers the needle; a housing that covers at least a base end part of the syringe; and a step part that is formed on an outer peripheral surface of the cap or between the housing and the cap, the step part protruding farther outward than a side surface of the barrel part. The step part is configured to engage with a lower surface of a notch part that extends laterally inward from an outer edge of a flange part of a container such that the cap is removable from the housing by the notch part.

In one embodiment, provided is a packaging body for housing a liquid injection device that comprises a syringe that has a barrel part configured to be filled with a liquid and a needle, attached to a distal portion of the barrel, configured to discharge the liquid, a cap that covers the needle, and a housing that covers at least a base end part of the syringe, the liquid injection device having a step part that is formed on an outer peripheral surface of the cap or between the housing and the cap, which protrudes farther outward than the side surface of the barrel part. The packaging body comprises a container comprising a housing space for housing the liquid injection device, and an opening for removing the liquid injection device from the housing space, the container being configured to be attached to a sealing member for sealing the opening. The container comprises an engaging part that engages with the step part so as to remove the cap from the liquid injection device.

In one aspect, the container has a bottom part, side wall parts that extend upward from a periphery of the bottom part, the opening surrounded by upper ends of the side wall parts, and a flange part that laterally extends from the upper ends of the side wall parts and is configured to be attached the sealing member. A notch part is provided at a part of the flange part, the notch part opening toward laterally. A lower end surface of the notch part functions as the engaging part.

In one aspect, the notch part is provided at a part covered with the sealing member.

In one aspect, the packaging body is configured to house the liquid injection device having an elongated shape. The opening has an elongated shape. The container has a shape having a long axis and a short axis in a plan view seen from a direction vertical to the bottom part such that the container is configured to house the liquid injection device in the housing space in a state that the axis of the liquid injection device is approximately parallel to a longitudinal direction of the opening. The notch part is provided at an end portion of the flange part in the direction of the long axis.

In one aspect, the packaging body is configured to house the liquid injection device having an elongated shape. A distance from the bottom part of the container to the flange part in a direction vertical to the bottom part is equal to or longer than a distance from a distal end of the cap to the step part in the axial direction of the liquid injection device.

In one aspect, the packaging body is configured to house the liquid injection device having an elongated shape. The notch part is provided to engage with parts of the step part that are facing across the axis of the liquid injection device.

In one aspect, the packaging body is configured to house the liquid injection device having an elongated shape. The step part is provided over a entire circumference around the axis of the liquid injection device. The notch part is formed to have a shape along the step part.

In one aspect, the container has a bottom part, side wall parts that extend upward from a periphery of the bottom part, the opening surrounded by the upper ends of the side wall parts, and a protruding part that protrudes to the housing space from a inner surfaces of the side wall parts. A lower end surface of the protruding part is apart from the bottom part in the direction vertical to the bottom part at a distance equal to or longer than a distance from the distal of the cap to the step part in the axial direction of the liquid injection device, and functions as the engaging part.

In one aspect, the packaging body is configured to house the liquid injection device having an elongated shape. The opening has an elongated shape. The container has a shape having a long axis and a short axis in a plan view seen from the direction vertical to the bottom part such that the container is configured to house the liquid injection device in the housing space in a state that the axis of the liquid injection device is approximately parallel to the longitudinal direction of the opening. The protruding part is provided at the vicinity of end parts of the side wall parts in the direction of the long axis.

In one aspect, the packaging body is configured to house the liquid injection device having an elongated shape. The opening has an elongated shape. The container has a shape having a long axis and a short axis in a plan view seen from the direction vertical to the bottom part such that the container is configured to house the liquid injection device in the housing space in a state that the axis of the liquid injection device is approximately parallel to the longitudinal direction of the opening. The protruding part is provided as at least a pair of protruding parts such that the protruding parts face to each other in the short axis direction and engage with parts of the step part that are facing across the axis of the liquid injection device.

In one aspect, the packaging body is configured to house the liquid injection device having an elongated shape. The opening has an elongated shape. The container has a shape having a long axis and a short axis in a plan view seen from the direction vertical to the bottom part such that the container is configured to house the liquid injection device in the housing space in a state that the axis of the liquid injection device is approximately parallel to the longitudinal direction of the opening. The container has a cap inserting part in the housing space adjacent to the protruding part in the long axis direction, the cap inserting part to which at least a part closer to the distal end than the step part of the cap can be inserted in a state that the axis of the liquid injection device and the bottom part are approximately vertical. The engaging part is configured to engage with the parts of the step part that are facing across the axis of the liquid injection device by moving the cap inserted in the cap inserting part toward the protruding part in the long axis direction.

In one aspect, the container has a movement restricting part on the opposite side of the long axis direction across the protruding part with respect to the cap inserting part, the movement restricting part restricting the movement of the cap inserted in the cap inserting part.

In one aspect, the protruding part is disposed at the vicinity of the opening.

In one aspect, the housing space has a cap housing space for housing the cap of the liquid injection device in the housing space, and the protruding part is disposed on the parts of the side wall parts that form the cap housing space.

In one aspect, the packaging body includes the sealing member.

In another embodiment, a packaging assembly includes the packaging body described above, and the liquid injection device housed in the housing space. The opening has been sealed with the sealing member.

According to certain embodiments of the present invention, when the cap is removed from a liquid injection device such as an auto injector, the cap can be removed easily and certainly by engaging a step part of the cap with engaging parts of a packaging body.

Furthermore, since the step part protrudes farther outward than the side surface of the barrel part, the step part can be easily engaged with the engaging parts.

DESCRIPTION OF EMBODIMENTS

The packaging body and packaging assembly of the present invention will be explained below in detail based on the exemplary embodiments shown in the attached drawings.

Figure 1:
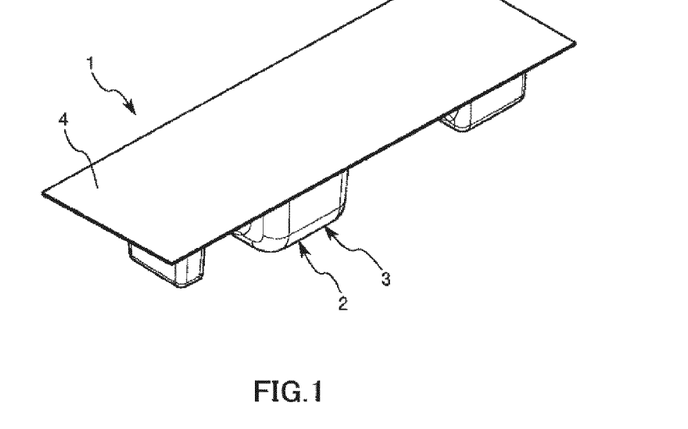
FIG. 1 is a perspective view showing an exemplary embodiment of the packaging assembly of the present invention.
Figure 2:
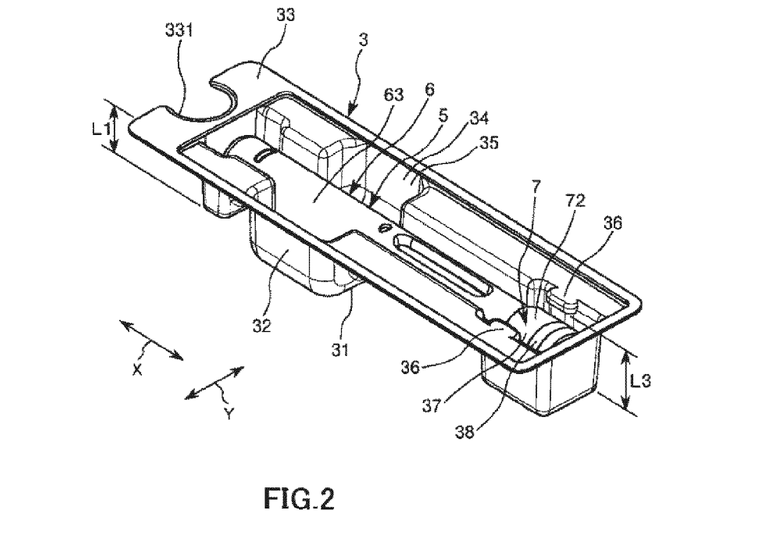
FIG. 2 is a perspective view showing a state in which the sealing member has been peeled from the packaging assembly shown in FIG. 1.

FIG. 1 is a perspective view showing an exemplary embodiment of the packaging assembly of the present invention. FIG. 2 is a perspective view showing a state in which the sealing member has been peeled from the packaging assembly shown in FIG. 1. FIGS. 3 to 5, 8 and 11 are each a perspective view for explaining an operation procedure in removing the cap of the packaging assembly shown in FIG. 1. FIGS. 9 and 10 are each a plane view for explaining an operation procedure in removing the cap of the packaging assembly shown in FIG. 1. FIGS. 6, 7, 12 and 13 are each a cross-sectional view for explaining an operation procedure in removing the cap of the packaging assembly shown in FIG. 1.

In the following explanation, for convenience of explanation, the terms "upper side," "lower side," "right side" and "left side" refer to the sides as shown in the Figures. Furthermore, for convenience of explanation, the left side of the liquid injection device as shown in FIG. 2 is also referred to as "base end" and the right side as shown in FIG. 2 is referred to as the "distal end." Similarly, the upper side as shown in FIGS. 3-8 and 11-13 is referred to as to "base end" and the lower side as shown in FIGS. 3-8 and 11-13 is referred to as the "distal end."

Furthermore, in FIGS. 6, 7, 12 and 13, the illustration of the plunger and second coil spring is omitted. Furthermore, in FIGS. 9 and 10, only the outermost periphery part (site) of the remover of the cap, i.e., the outer cylinder, is illustrated for the liquid injection device.

As shown in FIGS. 1 and 2, a packaging assembly 1 includes a liquid injection device 5, and a packaging body 2 for housing the liquid injection device 5.

The liquid injection device 5 is an auto injector having an elongated shape, which is filled with a drug solution (liquid) in advance, and is used in injecting (administering) the drug solution to a living body. The drug solution is not specifically limited, and is suitably selected from, depending on the purpose of use, for example, hematinics, vaccines, hormone formulations, antirheumatic agents, anticancer agents, anesthetic agents, anticoagulants and the like.

Figure 6:
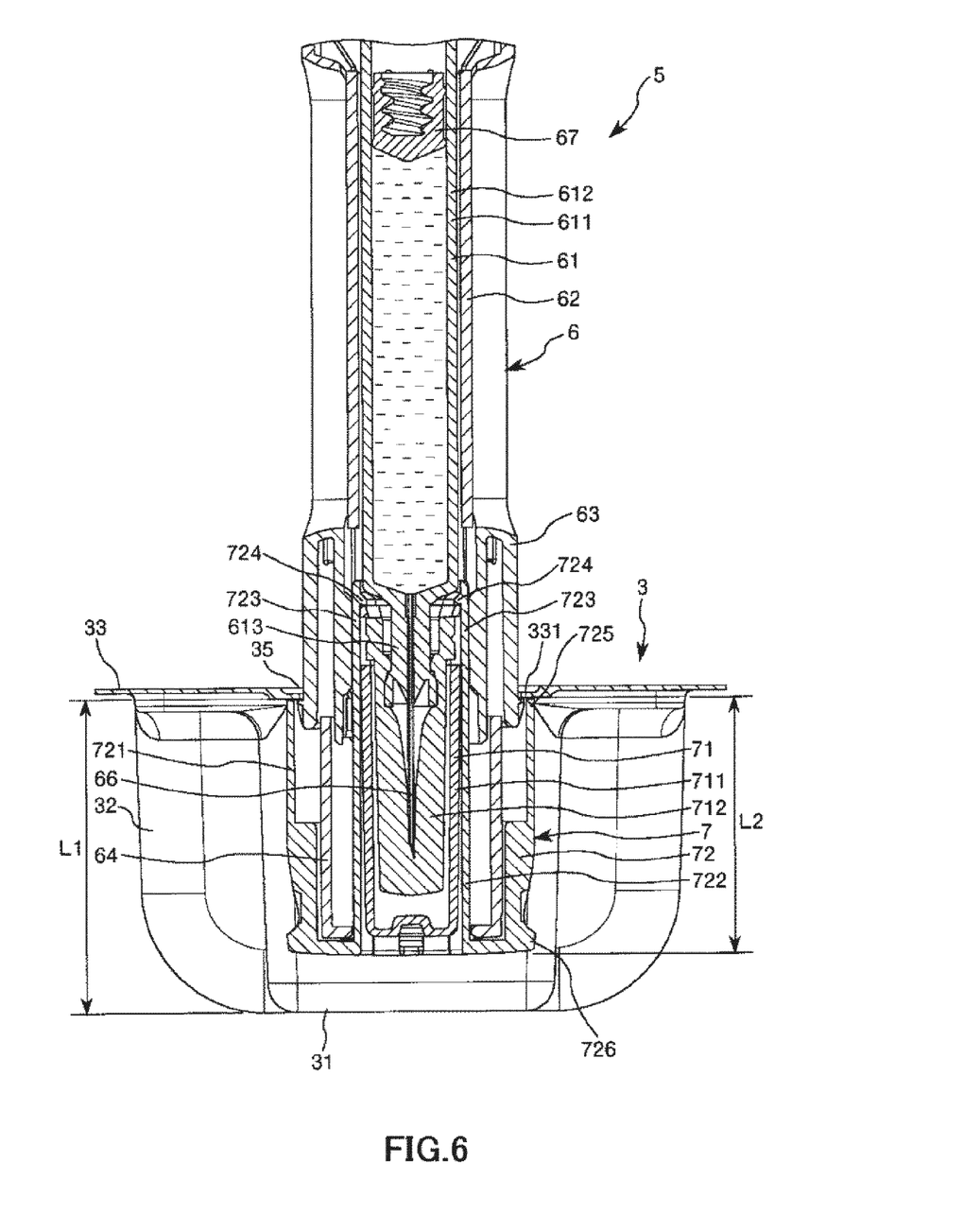
FIG. 6 is a cross-sectional view for explaining an operation procedure in removing the cap of the packaging assembly shown in FIG. 1.
Figure 7:
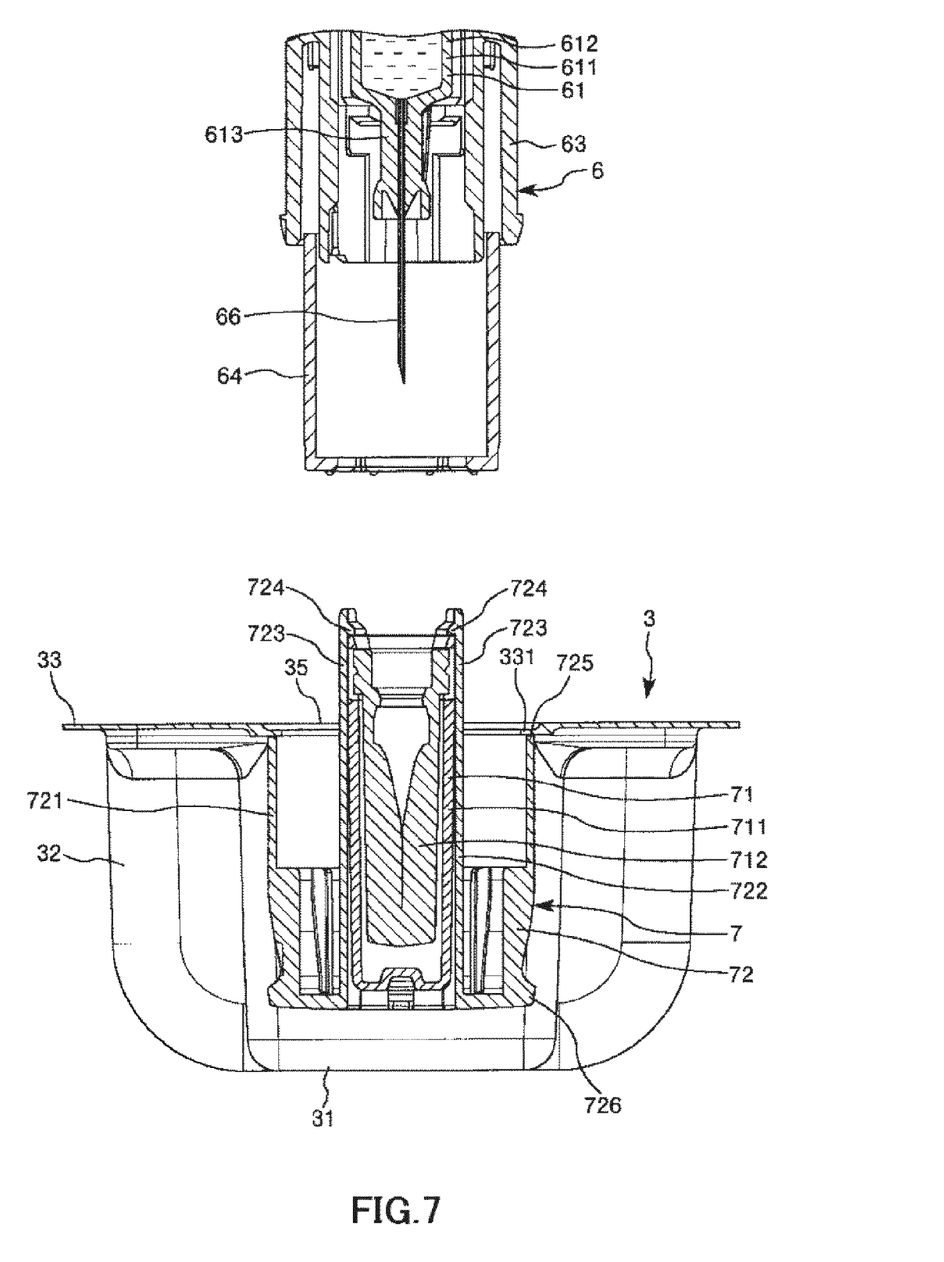
FIG. 7 is a cross-sectional view for explaining an operation procedure in removing the cap of the packaging assembly shown in FIG. 1.

As shown in FIGS. 2, 6 and 7, the liquid injection device 5 has a liquid injection device main body 6 having an elongated shape, and a cap 7 that is removably attached to the liquid injection device main body 6. Because the cap 7 is attached to the liquid injection device main body 6, a needle 66 (described below) of the liquid injection device main body 6 can be protected, and erroneous pricking by the needle 66, and the like can be prevented.

The liquid injection device main body 6 has a housing 63 having a cylindrical shape with a bottom, a syringe 61 disposed on the inner periphery side of the housing, a syringe holder 62 that holds the syringe 61, a needle cover 64 that covers at least a distal portion of a needle 66 of the syringe 61, a first coil spring, which is not illustrated, and a second coil spring, which is not illustrated. The syringe holder 62 is retained in the housing 63. Furthermore, the housing 63 covers a part other than the needle 66 of the syringe 61, i.e., a cylindrical body 611. This housing 63 is a gripping part for gripping in injecting a drug solution into a living body. It is sufficient that the housing 63 covers at least the base end part of the syringe 61.

The syringe 61 has a cylindrical shape with a bottom, and has a cylindrical body 611 capable of being filled with a drug solution, a needle (hollow needle) 66 configured to discharge the drug solution, which is attached to the distal portion of the cylindrical body 611, a gasket 67 being capable of sliding in the cylindrical body 611, which is disposed in the cylindrical body 611, and a plunger connected to the gasket 67, which is not illustrated. The first coil spring biases the gasket 67 toward the distal direction through the plunger. Furthermore, a retainer, which is not illustrated, is engaged with the plunger, and thus, the movement of the plunger in the distal direction is blocked.

The cylindrical body 611 has a barrel part 612 having a bottom part, and a diameter-reduced part 613, integral with the barrel part 612, that is disposed on the central part of the bottom part and whose diameter is reduced with respect to the barrel part 612. Furthermore, an opening through which a liquid can enter and be discharged is constituted by the diameter-reduced part 613. Furthermore, the needle 66 is attached (fixed) to the diameter-reduced part 613 disposed on the distal portion of the barrel part 612.

A drug solution is housed in advance in a lumen part of the cylindrical body 611, i.e., a space that is surrounded by the cylindrical body 611 and the gasket 67 and is located on the distal side of the gasket 67.

The needle 66 is a hollow needle tube having a sharp needle tip on the distal end, and can needle a living body with the needle tip. The lumen part of the needle 66 is in communication with the lumen part of the cylindrical body 611, and functions as a flow path through which the drug solution from the cylindrical body 611 passes. Using the needle tip of the needle 66, the needle is inserted into the living body up to a predetermined depth from the skin, and the drug solution is then injected into the body through the flow path of the needle 66.

The needle cover 64 has a distal opening, and is movably installed in the housing 63 in the axial direction of the liquid injection device 5. This needle cover 64 can be moved toward a first position (covering position) where at least the needle tip of the needle 66 is covered, and a second position (evacuation position) where the needle tip of the needle 66 is exposed. The second coil spring biases the needle cover 64 toward the distal direction so that the needle cover 64 is positioned on the first position and the distal opening of the needle cover 64 is positioned closer to the distal side than the needle tip of the needle 66.

When the drug solution is injected to a living body, the housing 63 of the liquid injection device 5 is gripped, the cap 7 is removed from the liquid injection device 5, and the distal portion of the needle cover 64 is pressed against an intended site on the surface of the living body. Thus, the needle cover 64 moves toward the base end direction in the second position, and the surface of the living body is needled by the needle tip of the needle 66. Furthermore, when the needle cover 64 has moved to the second position, the engaging of the retainer with the plunger is released, and the gasket 67 moves in the distal direction through the plunger by the biasing force of the first coil spring, and thus, the drug solution is discharged from the needle 66. Accordingly, according to this liquid injection device 5, since the gasket 67 automatically moves in the distal direction by the biasing force of the first coil spring, even a person having a weak grip, such as an aged person or a person who has difficulty in the fingers such as a patient suffering from rheumatism, can administer the drug solution in an easy and certain way.

The cap 7 has a needle shield member 71, and a remover 72 that is disposed on the outer periphery side of the needle shield member 71.

The needle shield member 71 has a needle tip protecting member 711 that covers the needle tip of the needle 66, and cover member 712 that retains the needle tip protecting member 711. The needle tip protecting member 711 is constituted by, for example, a rubber material, and is detachably attached to the diameter-reduced part 613 of the syringe 61. Furthermore, the opening of the needle tip of the needle 66 is sealed by the needle tip protecting member 711. The shapes of the needle tip protecting member 711 and the cover member 712 are not specifically limited, and have a cylindrical shape with a bottom in this exemplary embodiment.

The remover 72 has an outer cylinder 721, and an inner cylinder 722 that is disposed in a concentric manner with outer cylinder 721 on the inner side of the outer cylinder 721. Furthermore, a pair of arm parts 723 is formed on the base end of the inner cylinder 722 so as to protrude toward the base end side and face to each other across the axis of the liquid injection device 5. Furthermore, a claw 724 is formed on the base end part of each arm part 723 so that the claw 724 protrudes toward the axis of the liquid injection device 5.

The cover member 712 of the needle shield member 71 is disposed on the inner side of the inner cylinder 722, and is retained by the inner cylinder 722. Furthermore, the claw 724 of each arm part 723 engages with the base end of the cover member 712. Accordingly, when the cap 7 is removed from the liquid injection device 5, when the remover 72 moves in the distal direction with respect to the liquid injection device main body 6, the needle shield member 71 also moves in the together with the remover 72, and thus, the cap 7 can be removed.

This remover 72 is attached to the distal portion of the housing 63 of the liquid injection device main body 6. In this case, the base end part of the outer cylinder 721 fits with the outer periphery part of the distal portion of the housing 63, and the base end part of each arm part 723 fits with the inner periphery part of the distal portion of the housing 63. Accordingly, in the liquid injection device 5 in the state that the cap 7 is attached, the remover 72 is abutting with the inner peripheral surface and the outer peripheral surface of the distal portion of the housing 63. Therefore, when the cap 7 is removed from the liquid injection device 5, the bending of the remover 72 against the housing 63 can be blocked, and thus, the bending of the needle 66 with the cap 7 can be prevented.

Furthermore, a step part (first step part) 725 that protrudes farther outward than the side surface of the barrel part 612 is disposed between the housing 63 and the outer cylinder 721 of the remover 72 of the cap 7. This step part 725 is constituted by the base end part of the outer cylinder 721 and the like and is disposed in a circle around the axis of the liquid injection device 5, and engages with a notch part 331 or a pair of protruding parts 36 (described below) of the packaging body 2 when the cap 7 is removed from the engage liquid injection device 5.

Furthermore, a diameter-reduced part, which has a reduced diameter with respect to that of the base end part of the outer cylinder 721, and a diameter-expanded part, which has an expanded diameter with respect to that of the diameter-reduced part, are formed on the outer peripheral surface of the distal portion of the outer cylinder 721, and a step part (second step part) 726 that protrudes farther outward than the side surface of the barrel part 612 is disposed by the diameter-reduced part and the diameter-expanded part. This step part 726 is disposed on the outer peripheral surface of the outer cylinder 721 in a circle around the axis of the liquid injection device 5, and engages with a notch part 331 or a pair of protruding parts 36 (described below) of the packaging body 2, when the cap 7 is removed from the liquid injection device 5. In removing the cap 7 from the liquid injection device 5, either of the step part 725 and the step part 726 may be engaged with the notch part 331 or the protruding parts 36.

Furthermore, the cap 7 can be removed from the liquid injection device 5 by gripping the remover 72 with the fingers and withdrawing the remover 72 in the distal direction, and at this time, the step part 726 functions as a finger hooking part for hooking the fingers.

Next, the packaging body 2 will be explained.

As shown in FIGS. 1 and 2, the packaging body 2 includes a container 3 for housing the liquid injection device 5, and a sealing member 4 that is detachably attached to the container 3. The sealing member 4 is a sheet material having a sheet shape, i.e., a planar shape.

Figure 3:
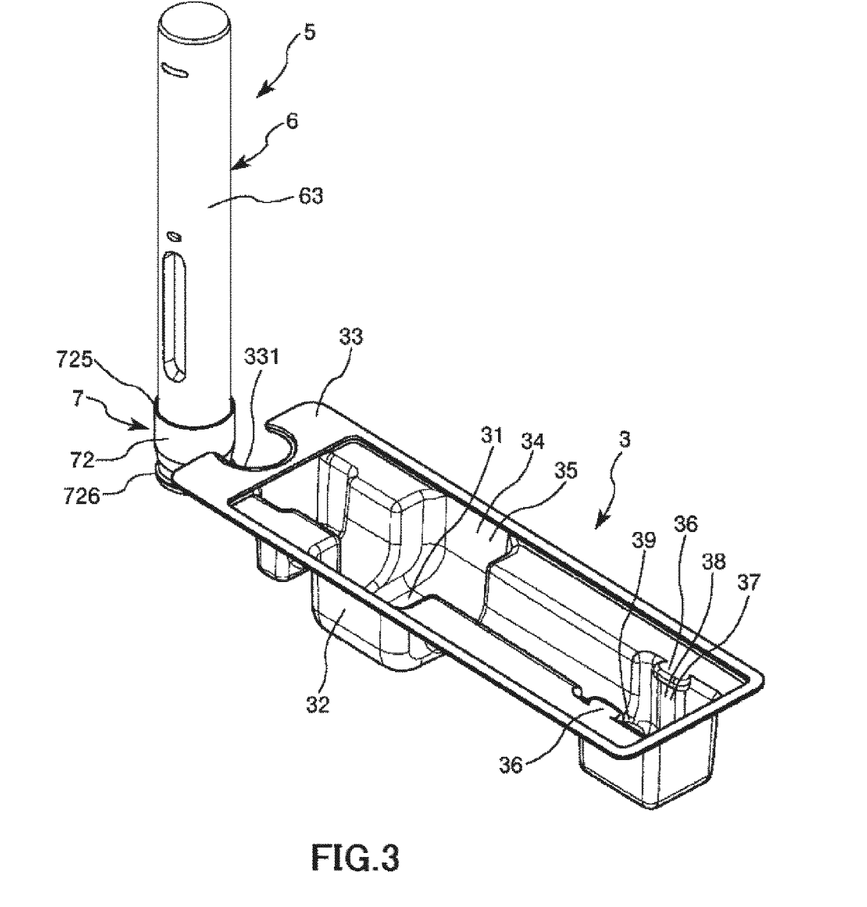
FIG. 3 is a perspective view for explaining an operation procedure in removing the cap of the packaging assembly shown in FIG. 1.

As shown in FIGS. 2 and 3, the container 3 is formed into a protruded shape (blister shape) in which the liquid injection device 5 can be housed, i.e., a housing space 34 for housing the liquid injection device 5 (described below) can be ensured. That is, the container 3 has a bottom part 31, side wall parts 32 that extend toward the upper side from a periphery of the bottom part 31, and a flange part 33 for attaching a sealing member 4, which laterally extends from the upper ends of the side wall parts 32. Furthermore, a housing space 34 for housing the liquid injection device 5 is formed in apart inside of the container 3 by the bottom part 31 and the side wall parts 32, and an opening 35 for taking the liquid injection device 5 from the housing space 34 is formed on the upper end of the housing space 34. In the housing space 34, the end part of the right side is a cap housing space 38 for housing the cap 7 of the liquid injection device 5. The opening 35 is surrounded by the upper ends of the side wall parts 32.

The shape of the container 3 is not specifically limited, and in this exemplary embodiment, the shape is an elongated shape having a long axis and a short axis in a plan view seen from the direction vertical to the bottom part 31 (hereinafter referred to as a plan view), i.e., an approximately rectangular shape. In FIG. 2, the direction of the above-described long axis is represented by "X", and the direction of the above-described short axis is represented by "Y".

Furthermore, the shape of the opening 35 is not specifically limited, and in this exemplary embodiment, the shape is an elongated shape having a long axis and a short axis in a plan view.

Furthermore, the shape of the housing space 34 is not specifically limited, and the shape is a shape such that the liquid injection device 5 can be housed in the housing space 34 in a state that the axis of the liquid injection device 5 is in approximately parallel with the longitudinal direction of the opening 35.

Furthermore, as described above, a flange part 33 is formed in a circle around the outer periphery part of the upper end part of the container 3. In this flange part 33, among the four sides, the part on the left side is formed to be larger than the other parts.

Furthermore, a notch part 331, which opens laterally, is formed on the end part of the flange part 33 in the long axis direction X of the container 3, i.e., the part at the left side of the flange part 33. The lower end surface of this notch part 331 functions as an engaging part that engages with a step part 725 or 726 of the cap 7 so as to remove the cap 7 from the liquid injection device 5 (see FIGS. 4 and 6). By allowing the liquid injection device 5 to laterally approach the notch part 331 this way, the step part 725 or 726 of the cap 7 can be easily engaged with the notch part 331. Furthermore, because the notch part 331 is formed on the end part of the flange part 33 in the long axis direction X of the container 3, when the cap 7 is removed from the liquid injection device 5, in the state that the liquid injection device 5 is gripped by the fingers of one hand and the step part 725 or 726 is engaged with the notch part 331, the container 3 can be surely pressed by the fingers of another hand, and thus, the cap 7 can be easily removed from the liquid injection device 5.

For the notch part 331, the relationship with the step part 725 or 726 will be explained below. Because the relationship between the notch part 331 and the step part 725 and the relationship between the notch part 331 and the step part 726 are similar, the relationship between the notch part 331 and the step part 725 will be typically explained.

The shape of the notch part 331 is not specifically limited as long as the shape is such that the lower end surface of the notch part 331 can be engaged with the step part 725, and it is preferable that the notch part 331 is disposed in a manner that the lower end surface (engaging part) of the notch part 331 can be engaged with parts facing across the axis of the liquid injection device 5 of the step part 725. Thus, when the cap 7 is removed from the liquid injection device 5, the liquid injection device 5 becomes difficult to rotate around the engaging of the notch part 331 with the step part 725, and thus the cap 7 can be surely removed. Furthermore, it is preferable that the notch part 331 is formed into a shape that follows the shape of the step part 725. Thus, the notch part 331 and the step part 725 are surely engaged, and thus the cap 7 can be removed more surely. In this exemplary embodiment, the notch part 331 has an arc shape.

Furthermore, the distance L1 from the bottom part 31 to the flange part 33 in the direction vertical to the bottom part 31 of the container 3 (see FIG. 6) is equal to or longer than the distance L2 from the distal end of the cap 7 to the step part 725 in the axial direction of the liquid injection device 5 (see FIG. 6). Thus, when the cap 7 is removed from the liquid injection device 5, the step part 725 can be disposed on the lower side of the notch part 331 in the state that the container 3 is placed on a table or the like with aiming the bottom part 31 downward in the perpendicular direction without lifting the container 3, and thus the step part 725 can be easily engaged with the notch part 331.

Furthermore, the upper surface of the flange part 33 is a site to which the sealing member 4 can be attached, and the sealing member 4 is detachably attached to the upper surface of the flange part 33 by, for example, fusion bonding or adhesion or the like. Thus, the flange part 33 is covered with the sealing member 4, and the opening 35 is tightly sealed, and thus a sterilized state inside of the packaging body 2 can be maintained.

Furthermore, when the sealing member 4 is peeled from the packaging body 2, the sealing member 4 can be easily peeled by gripping the part corresponding to the missing part of the notch part 331 in the sealing member 4.

Furthermore, the container 3 has a pair of protruding parts 36 protruding from the inner surfaces of the side wall parts 32 to the housing space 34. The lower end surface of each protruding part 36 functions as an engaging part that engages with the step part 725 or 726 of the cap 7 so as to remove the cap 7 from the liquid injection device 5 (see FIG. 10 and FIG. 12). The number of the protruding parts 36 is not limited to two, and may also be, for example, one, or three or more, and is preferably two or more. Because each protruding part 36 is disposed on the housing space 34, in the case when the cap 7 is removed from the liquid injection device 5, the cap 7 is housed in the housing space 34. Therefore, the cap 7 is easily disposed without rolling or the like.

In the following description, when the relationships with the step part 725 and 726 are explained for the protruding part 36, because the relationship between the protruding part 36 and the step part 725 and the relationship between the protruding part 36 and the step part 726 are similar, the relationship between the protruding part 36 and the step part 725 will be commonly explained.

Figure 12:
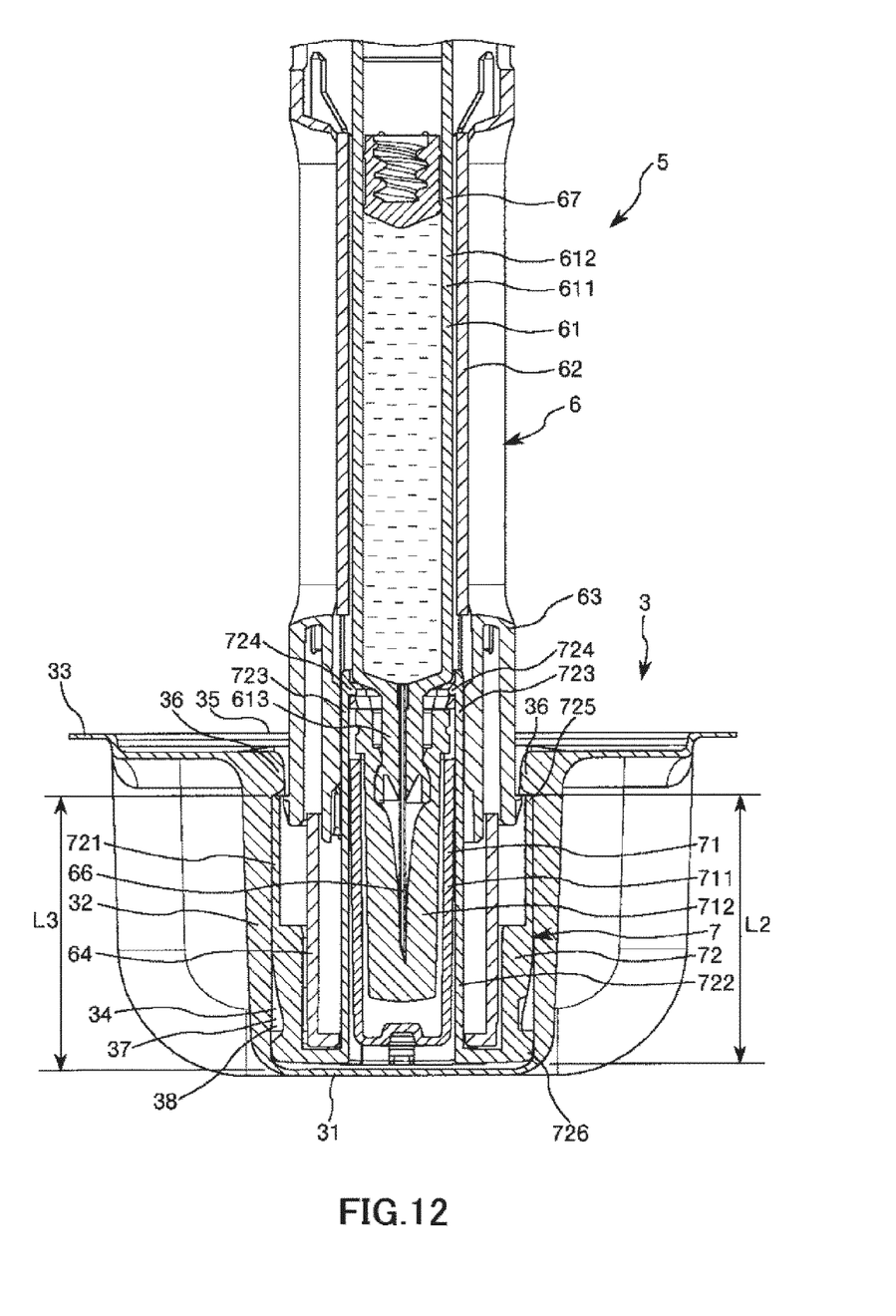
FIG. 12 is a cross-sectional view for explaining an operation procedure in removing the cap of the packaging assembly shown in FIG. 1.

The lower end surface of each protruding part 36 is apart from the bottom part 31 at a distance equal to or longer than the distance L2 from the distal end of the cap 7 to the step part 725 in the direction vertical to the bottom part 31 (see FIG. 12). That is, the distance L3 from the bottom part 31 to each protruding part 36 in the direction vertical to the bottom part 31 of the container 3 (see FIG. 12) is equal to or longer than the distance L2. Thus, when the cap 7 is removed from the liquid injection device 5, the step part 725 can be disposed on the lower side of the protruding part 36 in the state that the cap 7 is inserted into the part where the protruding parts 36 have been formed of the housing space 34, without deforming the container 3, and thus, the step part 725 can be easily engaged with the notch part 331.

Furthermore, the protruding parts 36 are disposed so that the protruding parts 36 face to each other in the short axis direction Y of the container 3 (see FIG. 2) and the lower end surfaces (engaging parts) of the protruding parts 36 can be engaged with the parts that face across the axis of the liquid injection device 5 of the step part 725 (see FIG. 10). Thus, when the cap 7 is removed from the liquid injection device 5, the liquid injection device 5 becomes difficult to rotate around the engaging of the notch part 331 with the step part 725, and thus the cap 7 can be surely removed.

Furthermore, the position of each protruding part 36 is not specifically limited, and in this exemplary embodiment, each protruding part 36 is disposed in the vicinity of the end part of the side wall part 32 in the long axis direction X of the container 3. Thus, when the cap 7 is removed from the liquid injection device 5, in the state that the liquid injection device 5 is gripped by the fingers of one hand and the step part 725 is engaged with each protruding part 36, the container 3 can be surely pressed by the fingers of another hand, and thus, the cap 7 can be easily removed from the liquid injection device 5. Furthermore, each protruding part 36 is disposed in the vicinity of the opening 35. Thus, a user can easily recognize the respective protruding parts 36. Furthermore, the respective protruding parts 36 are disposed on the cap housing space 38. Thus, a user can easily understand that the respective protruding parts 36 are used in removing the cap 7.

Furthermore, the container 3 has a cap inserting part 37 to which, when the cap 7 is removed from the liquid injection device 5, at least a part closer to the distal end than the step part 725 of the cap 7 can be inserted in a state that the axis of the liquid injection device 5 and the bottom part 31 is approximately vertical. The cap inserting part 37 is disposed in the housing space 34 adjacent to the respective protruding parts 36 in the long axis direction X of the container 3, i.e., a cap housing space 38.

Figure 8:
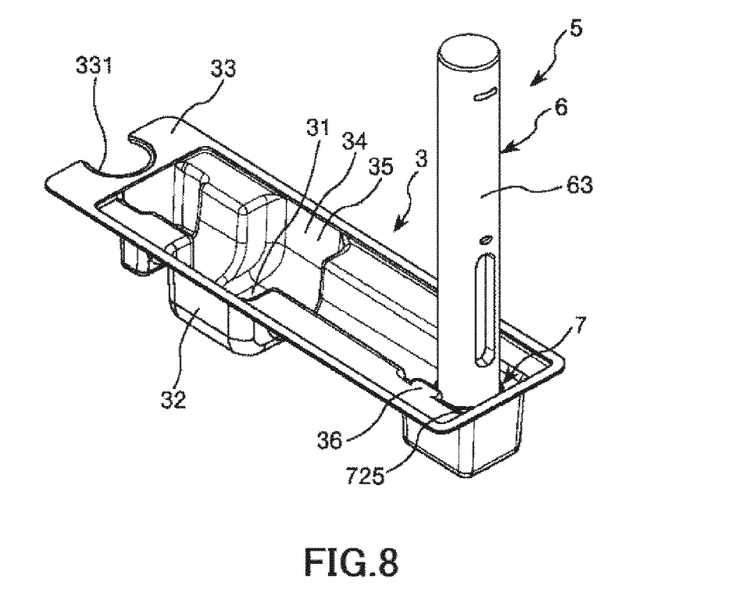
FIG. 8 is a perspective view for explaining an operation procedure in removing the cap of the packaging assembly shown in FIG. 1.
Figure 9:
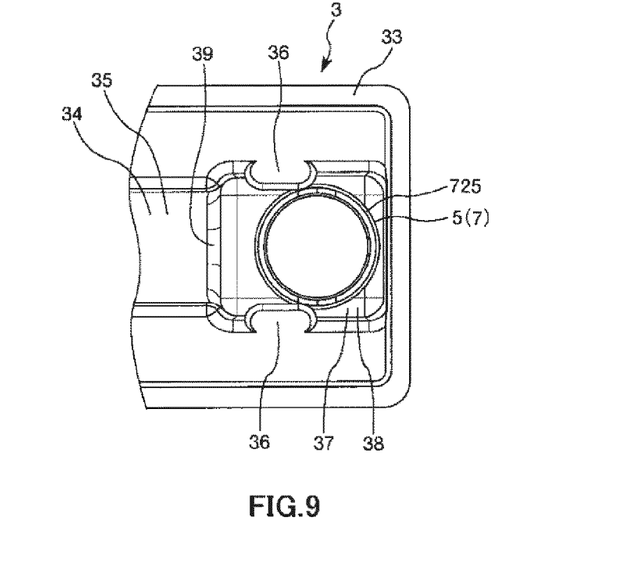
FIG. 9 is a plane view for explaining an operation procedure in removing the cap of the packaging assembly shown in FIG. 1.
Figure 10:
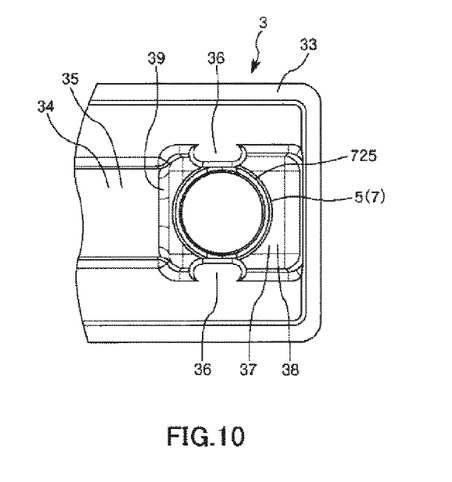
FIG. 10 is a plane view for explaining an operation procedure in removing the cap of the packaging assembly shown in FIG. 1.

When the cap 7 is removed from the liquid injection device 5, as shown in FIGS. 8 and 9, the cap 7 of the liquid injection device 5 is inserted in the cap inserting part 37 and moved toward the respective protruding parts 36 in the long axis direction X of the container 3 (toward the left side in FIG. 9) in the state that the axis of the liquid injection device 5 and the bottom part 31 are approximately vertical. Thus, as shown in FIGS. 10 and 12, the lower end surfaces of the respective protruding parts 36 become possible to engage with the parts that face across the axis of the liquid injection device 5 of the step part 725. Accordingly, when the cap 7 is inserted in the cap housing space 38 and the step part 725 is disposed on the lower sides of the respective protruding parts 36 so as to remove the cap 7 from the liquid injection device 5, crushing or damaging of the protruding parts 36 by the cap 7 can be suppressed, and thus the respective protruding parts 36 can be surely engaged with the step part 725.

Furthermore, as shown in FIGS. 3, 9 and 10, the container 3 has a movement restricting part 39 that restricts the movement of the cap 7 inserted in the cap inserting part 37 with respect to the cap inserting part 37. This movement restricting part 39 is a step part disposed on the bottom part 31, and pinches the respective protruding parts 36 to thereby restrict the movement of the cap 7 to the opposite side in the long axis direction X of the container 3. That is, the movement restricting part 39 abuts to the cap 7 to thereby block the movement of the cap 7 when the liquid injection device 5 is moved to the left side in FIG. 9 from the state that the step part 725 of the cap 7 is not engaged with the respective protruding parts 36 (see FIGS. 8 and 9) to the state that the step part 725 can engage with the respective protruding parts 36 (see FIG. 10). Thus, the step part 725 and the respective protruding parts 36 can be engaged in an easy and surely manner.

Furthermore, the constitutional material of the container 3 is not specifically limited, and examples include various resins such as paper, polyvinyl chloride, polyethylene, polypropylene, polystyrene, poly-(4-methylpentene-1), polycarbonates, acrylic resins, acrylonitrile-butadiene-styrene copolymers, polyesters such as polyethylene telephthalate, butadiene-styrene copolymers and polyamides, and the like.

Secondly, the operational procedures for removing the cap 7 from the liquid injection device 5 of the packaging assembly 1 will be explained.

This packaging assembly 1 has two types of methods utilizing the container 3, besides the method in which the cap 7 is gripped and withdrawn in the distal direction, as the methods for removing the cap 7. A user of the liquid injection device 5 can select either one method from the two ways of methods. The two types of methods utilizing the container 3 will be sequentially explained below.

Firstly, as shown in FIG. 2, the sealing member 4 is peeled from the packaging body 2 of the packaging assembly 1, and as shown in FIG. 3, the liquid injection device 5 is taken from the container 3.

Figure 4:
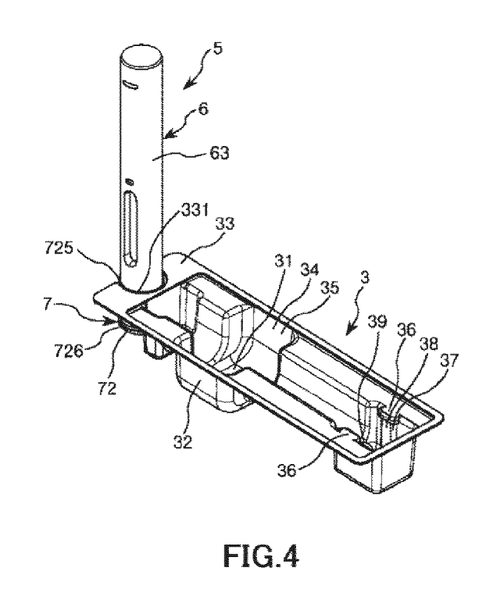
FIG. 4 is a perspective view for explaining an operation procedure in removing the cap of the packaging assembly shown in FIG. 1.
Figure 5:
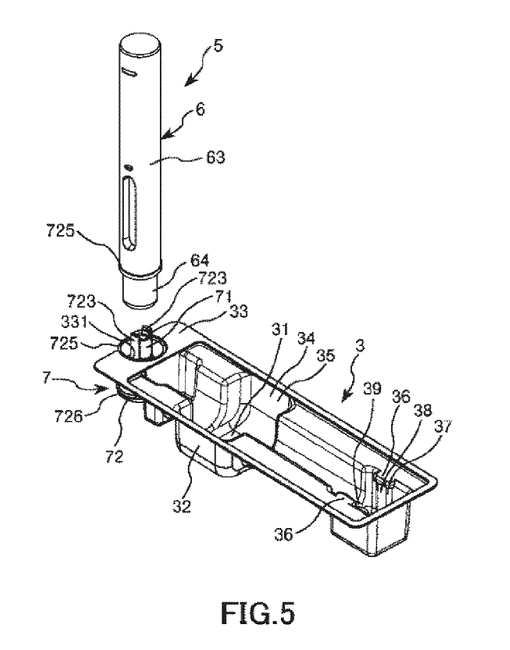
FIG. 5 is a perspective view for explaining an operation procedure in removing the cap of the packaging assembly shown in FIG. 1.

In the first method, subsequently, as shown in FIGS. 4 and 6, the step part 725 of the cap 7 is engaged with the notch part 331 of the container 3 in the state that the axis of the liquid injection device 5 and the flange part 33 (bottom part 31) are approximately vertical. The step part 726 may be engaged with the notch part 331 instead of the step part 725. Furthermore, as shown in FIGS. 5 and 7, with pressing the container 3 by the fingers of one hand, the liquid injection device 5 is gripped by the fingers of another hand and moved upward (the hands and fingers are not illustrated). Thus, the cap 7 is detached from the liquid injection device 5.

Figure 11:
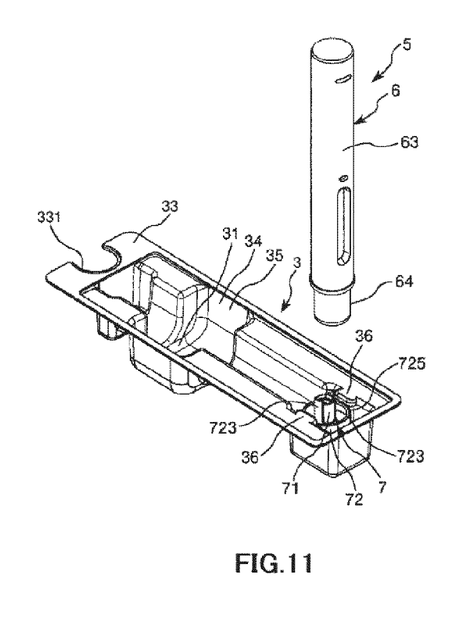
FIG. 11 is a perspective view for explaining an operation procedure in removing the cap of the packaging assembly shown in FIG. 1
Figure 13:
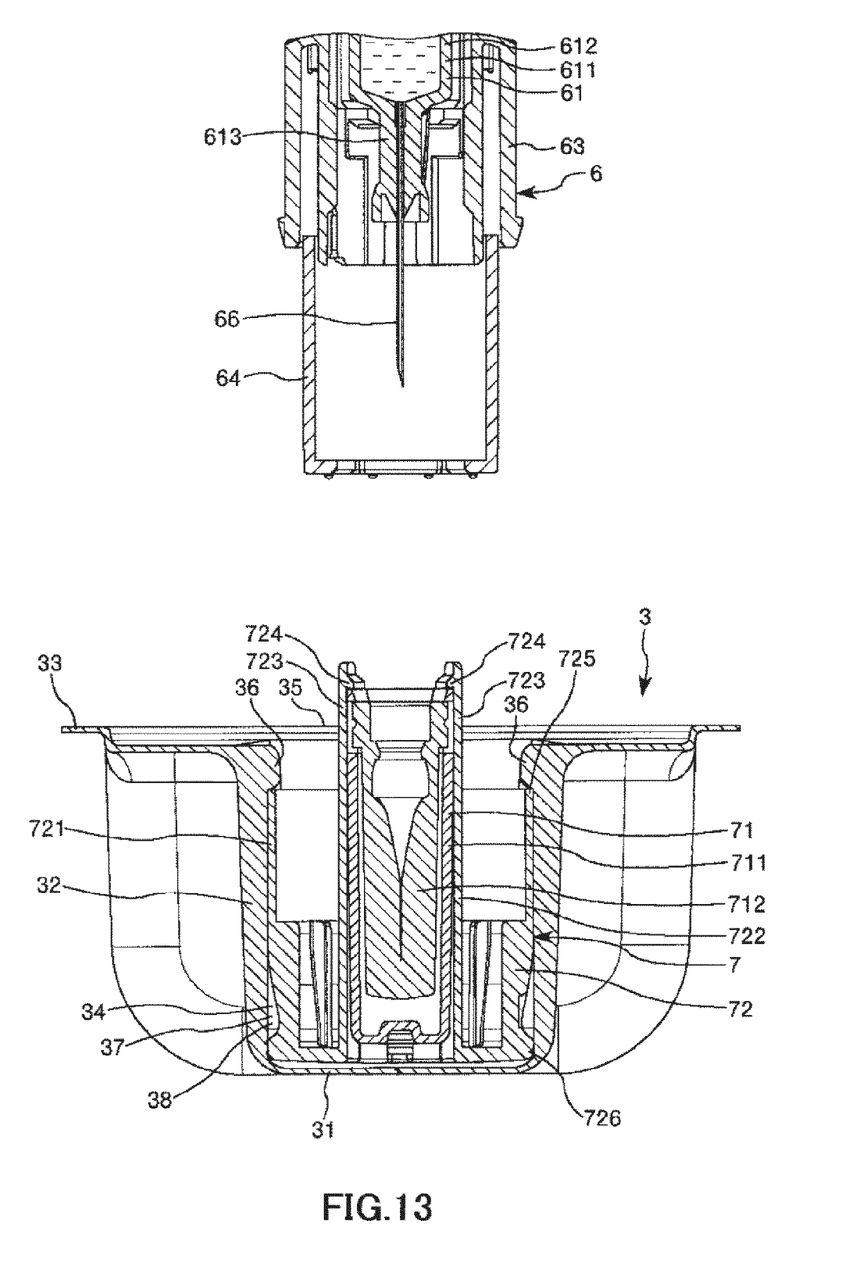
FIG. 13 is a cross-sectional view for explaining an operation procedure in removing the cap of the packaging assembly shown in FIG. 1.

In the second method, the liquid injection device 5 is removed from the container 3, the step part 725 of the cap 7 is then engaged with the respective protruding parts 36 of the container 3, as shown in FIGS. 10 and 12. In this case, firstly, as shown in FIGS. 8 and 9, the cap 7 of the liquid injection device 5 is inserted in a place that is closer to the right side in FIG. 9 than the respective protruding parts 36 of the cap inserting part 37, in the state that the axis of the liquid injection device 5 and the bottom part 31 are approximately vertical, and the cap 7 is moved to the left side in FIG. 9. Thus, as shown in FIGS. 10 and 12, the respective protruding parts 36 become possible to engage with the step part 725. Instead of the step part 725, the step part 726 may be put into a state being capable of engaging with the respective protruding parts 36. Furthermore, as shown in FIGS. 11 and 13, with pressing the container 3 by the fingers of one hand, the liquid injection device 5 is gripped by the fingers of another hand and moved toward the upper side (the hands and fingers are not illustrated). Thus, the protruding part 36 engage with the step part 725, and the cap 7 is detached from the liquid injection device 5.

As explained above, according to this packaging assembly 1, when the cap 7 is removed from the liquid injection device 5, by allowing the step part 725 or 7265 of the cap 7 to engage with the notch part 331 or the respective protruding parts 36 of the packaging body 2, even a person having a weak grip such as an aged person or a person who has difficulty in the fingers such as a patient suffering from rheumatism can remove the cap 7 in an easy and certain way.

Furthermore, because the step parts 725 and 726 protrude farther outward than the side surface of the barrel part 612 of the syringe 61, the step part 725 or 726 can be easily engaged with the notch part 331 or the respective protruding parts 36.

The packaging body and packaging assembly of the present invention have been explained based on the illustrated exemplary embodiments. However, the present invention is not limited to these embodiments, and each part can be substituted with a part having an optional constitution capable of exerting a similar function. Furthermore, optional constitutional matters may also be added.

Furthermore, embodiments of the present invention may be a combination of optional two or more constitutions (features) among the above-described respective exemplary embodiments.

In addition, in embodiments of the present invention, either the notch part or the protruding parts may be omitted.

Furthermore, the protruding parts are provided with an aim of being engaged with the step part (first step part) formed between the housing and the cap in the above-described exemplary embodiments. However, the present invention is not limited to these exemplary embodiments, and the protruding parts may be provided with an aim of being engaged with the step part (second step part) formed on the outer peripheral surface of the cap. In this case, it is sufficient that the distance from the bottom part to the protruding parts in the direction vertical to the bottom part of the container is equal to or longer than the distance from the distal end of the cap to the second step part.

Furthermore, the packaging body has a sealing member for sealing the opening of the container in the above-described exemplary embodiments. However, the present invention is not limited to this constitution, and may have, for example, a constitution having no sealing member and having a housing box for housing the container. In this case, it is preferable that the housing box houses the container in a slidable manner. In addition, the packaging body may also have a constitution having both a sealing member and a housing box.

Furthermore, the cap is constituted by the remover and the needle shield member in the above-described exemplary embodiments. However, the present invention is not limited to this constitution, and for example, the remover may be omitted. In this case, a step part protruding farther outward than the side surface of the barrel part is provided on the outer peripheral surface of the needle shield member or between the housing and the needle shield member.

Furthermore, the liquid injection device is an auto injector in the above-described exemplary embodiments. However, the present invention is not limited to this form, and for example, the form may be such that a liquid is discharged by manually pressurizing a plunger.

Furthermore, the liquid injection device has a constitution in which the drug solution is housed in the syringe in advance in the above-described exemplary embodiments, but the constitution is not limited to these, and for example, a drug as a solid formulation such as a powdered formulation may be housed in the syringe. In this case, a liquid such as a lysate is injected into the syringe at the time of use, and a solution formed by dissolving a drug in the liquid can be used as the "drug solution". Furthermore, the liquid injection device may also have a form that is not filled with a liquid in advance.

The packaging body of one embodiment the present invention is a packaging body for housing a liquid injection device including a barrel part capable of being filled with a liquid, a syringe having a needle for discharging the liquid, which is attached to a distal portion of the barrel part, a cap that covers the needle, and a housing that covers at least a base end part of the syringe, the liquid injection device having a step part protruding farther outward than the side surface of the barrel part between an outer peripheral surface of the cap or the housing and the cap. The packaging body includes a container including a housing space for housing the liquid injection device and an opening for removing the liquid injection device from the housing space, to which a sealing member for sealing the opening can be attached. The container included an engaging part that engages with the step part so as to remove the cap from the liquid injection device.

Furthermore, the packaging assembly of one embodiment the present invention is a packaging assembly, including the packaging body described above, and the liquid injection device housed in the housing space, where the opening has been sealed with the sealing member.

According to certain embodiments of the present invention, when the cap is removed from the liquid injection device, such as an auto injector, the cap can be removed in an easy and certain way, by allowing the step part of the cap to engage with the engaging part of the packaging body. Furthermore, because the step part protrudes farther outward than the side surface of the barrel part, the step part can be easily engaged with the engaging part. Therefore, the present invention has industrial applicability.

1 packaging assembly
2 packaging body
3 container
31 bottom part
32 side wall part
33 flange part
331 notch part
34 housing space
35 opening
36 protruding part
37 cap inserting part
38 cap housing space
39 movement restricting part
4 sealing member
5 liquid injection device
6 liquid injection device main body
61 syringe
611 cylindrical body
612 barrel part
613 diameter-reduced part
62 syringe holder
63 housing
64 needle cover
66 needle
67 gasket
7 cap
71 needle shield member
711 needle tip protecting member
712 cover member
72 remover
721 outer cylinder
722 inner cylinder
723 arm part
724 claw
725, 726 step parts

What is claimed is:

1. An assembly comprising:
   a liquid injection device, comprising:
      a syringe that comprises a barrel part configured to be filled with a liquid, and a needle attached to a distal portion of the barrel part and configured to discharge the liquid,
      a cap that covers the needle,
      a housing that covers at least a base end part of the syringe, and
      a step part that is formed on an outer peripheral surface of the cap or between the housing and the cap, the step part protruding farther outward than a side surface of the barrel part; and
   a packaging body comprising:
      a container comprising:
         a bottom part,
         side wall parts that extend upward from a periphery of the bottom part,
         a flange part, which extends laterally from upper ends of the side wall parts,
         a housing space defined by the bottom part and the side wall parts, the housing space housing the liquid injection device,
         an opening configured to allow removal of the liquid injection device from the housing space, the opening being surrounded by the upper ends of the side wall parts, and
         a notch part, which extends laterally inward from an outer edge of the flange part so as to define a notch, wherein a lower surface of the notch part is configured to engage with the step part of the liquid injection device so as to be usable to assist in removal of the cap from the liquid injection device, and
         a sealing member attached to the flange part of the container so as to seal the opening, wherein the sealing member covers the notch part.

2. The assembly according to claim 1,
   wherein the liquid injection device has an elongated shape,
   wherein the opening has an elongated shape,
   wherein the container has a shape having a long axis and a short axis in a top plan view,
   wherein the container houses the liquid injection device in the housing space in a state in which an axis of the liquid injection device is approximately parallel to a longitudinal direction of the opening, and
   wherein the notch part is provided at an end portion of the flange part corresponding to an end of the long axis of the container.

3. The assembly according to claim 1,
   wherein the liquid injection device has an elongated shape, and
   wherein a distance from the bottom part of the container to the flange part in a vertical direction is greater than or equal to a distance from a distal end of the cap to the step part in an axial direction of the liquid injection device.

4. The assembly according to claim 1,
   wherein the liquid injection device has an elongated shape, and
   wherein the notch part is configured to engage with parts of the step part that face each other across an axis of the liquid injection device.

5. The assembly according to claim 1,
wherein the liquid injection device has an elongated shape in which the step part is provided over an entire circumference around an axis of the liquid injection device, and
wherein a peripheral shape of the notch part corresponds to a peripheral shape of the step part, such that a periphery of the notch part extends along a periphery of the step part.

6. A method for removing a cap from a liquid injection device, the method comprising:
providing an assembly comprising:
a liquid injection device comprising:
a syringe that comprises a barrel part configured to be filled with a liquid, and a needle attached to a distal portion of the barrel part and configured to discharge the liquid,
a cap that covers the needle,
a housing that covers at least a base end part of the syringe, and
a step part that is formed on an outer peripheral surface of the cap or between the housing and the cap, the step part protruding farther outward than a side surface of the barrel part, and
a packaging body comprising:
a container comprising:
a bottom part,
side wall parts that extend upward from a periphery of the bottom part,
a flange part that extends laterally from upper ends of the side wall parts,
a housing space defined by the bottom part and the side wall parts, the housing space housing the liquid injection device,
an opening configured to allow removal of the liquid injection device from the housing space, the opening being surrounded by the upper ends of the side wall parts, and
a notch part that extends laterally inward from an outer edge of the flange part so as to define a notch, wherein a lower surface of the notch part is configured to engage with the step part of the liquid injection device so as to be usable to assist in removal of the cap from the liquid injection device, and
a sealing member attached to the flange part of the container so as to seal the opening, wherein the sealing member covers the notch part;
removing the liquid injection device from the housing space through the opening of the container;
disposing the step part of the liquid injection device below the notch part of the container in a state that the container is placed with the bottom part being downward and the opening being upward;
moving the injection device upward by a first hand while holding the container by a second hand so as to engage the notch part of the container with the step part of the liquid injection device; and
removing the cap from the injection device by further moving the injection device upward by the first hand while holding the container by the second hand.

* * * * *